(12) United States Patent
Crook

(10) Patent No.: US 6,856,253 B1
(45) Date of Patent: Feb. 15, 2005

(54) PERSONAL HYDROGEN SULFIDE GAS ALARM SYSTEM

(76) Inventor: Gary W. Crook, 2516 Seaboard, Midland, TX (US) 79705

( * ) Notice: Subject to any disclaimer, the term of this patent is extended or adjusted under 35 U.S.C. 154(b) by 20 days.

(21) Appl. No.: 10/640,809

(22) Filed: Aug. 14, 2003

(51) Int. Cl.[7] .............................................. G08B 17/10
(52) U.S. Cl. ............. 340/632; 340/539.11; 340/539.26; 73/23.2
(58) Field of Search ............................ 340/632, 10.52, 340/10.1, 573.1, 539.11, 539.13, 539.22, 539.26, 506; 73/23.2, 31.01, 31.02, 31.03

(56) References Cited

U.S. PATENT DOCUMENTS

| | | | | |
|---|---|---|---|---|
| 4,157,283 A | * | 6/1979 | Zetter | 205/786.5 |
| 5,454,918 A | * | 10/1995 | Javadi et al. | 205/786.5 |
| 5,867,105 A | * | 2/1999 | Hajel | 340/691.3 |
| 6,079,490 A | | 6/2000 | Newman | 166/77.51 |
| 6,252,510 B1 | | 6/2001 | Dungan | 340/632 |
| 6,606,897 B1 | * | 8/2003 | Koyano et al. | 73/23.2 |
| 6,744,373 B2 | * | 6/2004 | Koyano et al. | 340/693.5 |

* cited by examiner

*Primary Examiner*—Phung Nguyen
(74) *Attorney, Agent, or Firm*—Robert J. Harter

(57) ABSTRACT

A person-carried hydrogen sulfide instrument is adapted for use with a conventional SCADA system or other type of fault monitoring system normally intended for monitoring well-related conditions at a well site. In response to detecting an abnormally high concentration of hydrogen sulfide gas, the instrument triggers the fault monitoring system to record an H2S fault and convey that information to a remote computer. In some embodiments, the instrument includes a signal relay unit that listens to a conventional H2S monitor. The signal relay unit has a learning mode that teaches the unit to recognize an audible alarm from the H2S monitor. In response to hearing the H2S alarm, the signal relay unit emits a trigger signal to the fault monitoring system.

20 Claims, 1 Drawing Sheet

PERSONAL HYDROGEN SULFIDE GAS ALARM SYSTEM

BACKGROUND OF THE INVENTION

1. Field of the Invention

The subject invention pertains to the hazards of hydrogen sulfide and more specifically to a personal system for responding to an excessive amount of hydrogen sulfide.

2. Description of Related Art

Hydrogen sulfide, H2S, is a toxic gas that often accompanies the production of gas, oil and water. H2S can usually be contained, but if it escapes, an H2S monitor can be used for alerting personnel in the area. In response to sensing about 10 to 20 ppm of H25, typical H2S monitors will sound an alarm that warns of the danger. Once the alarm sounds, personnel often have sufficient time to vacate the area. In some cases, however, someone or everyone in the area may be overcome by the gas and fall to the ground. Since H2S is heavier than air, an unconscious person lying on the ground may continue breathing the toxic gas. If outside help is not quickly summoned to the area, eventually those continuing to breath the gas may die.

U.S. Pat. No. 6,252,510 discloses an H2S system that calls for outside help upon sensing an excessive amount of H2S at a distant location. The system appears to be designed for an established chemical plant where the H2S monitor is at a fixed, known location. Such a system may be fine for monitoring hydrogen sulfide gas at a particular location, but it may be inadequate for protecting an individual moving from one location to another.

In the case of an outdoor well site that includes a stationary H2S monitor, an undetected problem may occur if a hydrogen sulfide leak is downwind of the H2S monitor, and an oilfield worker is downwind of the leak. The worker may be exposed to the hydrogen sulfide gas, but the monitor may fail to detect the leak.

Today, H2S monitors, various fault monitoring systems, and wireless communications are used for monitoring conditions at a well site. SCADA (Supervisory Control And Data Acquisition) is perhaps the most common system for monitoring the pumping conditions at a well site and for communicating pumping-related faults to another location. Various transducers that sense a pumping condition (e.g., fluid pressure, fluid level, power failure, etc.) are hardwired to the hardware portion of the SCADA system. Hardwiring a person-carried H2S monitor to a SCADA system, unfortunately, would drastically limit the portability of the H25 monitor. Thus, person-carried H2S monitors are generally stand-alone devices that simply sound an alarm upon sensing a certain concentration of hydrogen sulfide gas. Such an alarm, however, may not necessarily alert outside help.

Consequently, a need exists for a completely portable, person-carried H2S monitor that can summon help from a remote location. It may be beneficial to have such a system where an existing conventional H2S monitor can be incorporated into a conventional SCADA system, thereby avoiding the cost of an entirely new monitor and communication system.

SUMMARY OF THE INVENTION

It is an object of some embodiments to provide a person-carried H2S monitor that communicates with a stationary fault monitoring system, which in turn communicates with a distant host computer.

It is an object of some embodiments to provide a personal alarm system where an existing conventional H2S monitor can be incorporated into a conventional SCADA system, thereby avoiding the cost of an entirely new monitor and communication system.

It is an object of some embodiments to use a microphone to help communicate an H2S fault to a fault monitoring system such as a SCADA system.

It is an object of some embodiments to provide a signal relay unit with a leaning mode so that the unit can adapt itself to different types of H2S monitors.

It is an object of some embodiments to provide a signal relay unit with a leaning mode for learning and storing multiple audible alarm patterns so that the unit can respond to a variety of H2S monitors.

It is an object of some embodiments to store the occurrence of an H2S fault event until a host computer pings the fault monitoring system.

It is an object of some embodiments to send an inquiry signal or ping a fault monitoring system to establish the location of where an H2S fault may have occurred.

It is an object of some embodiments to use a SCADA or other type of fault monitoring system to monitor pumping-related faults at fixed locations within a well site and to monitor H2S-related faults at indeterminate locations within the well site.

DESCRIPTION OF THE PREFERRED EMBODIMENT

Figure 1:
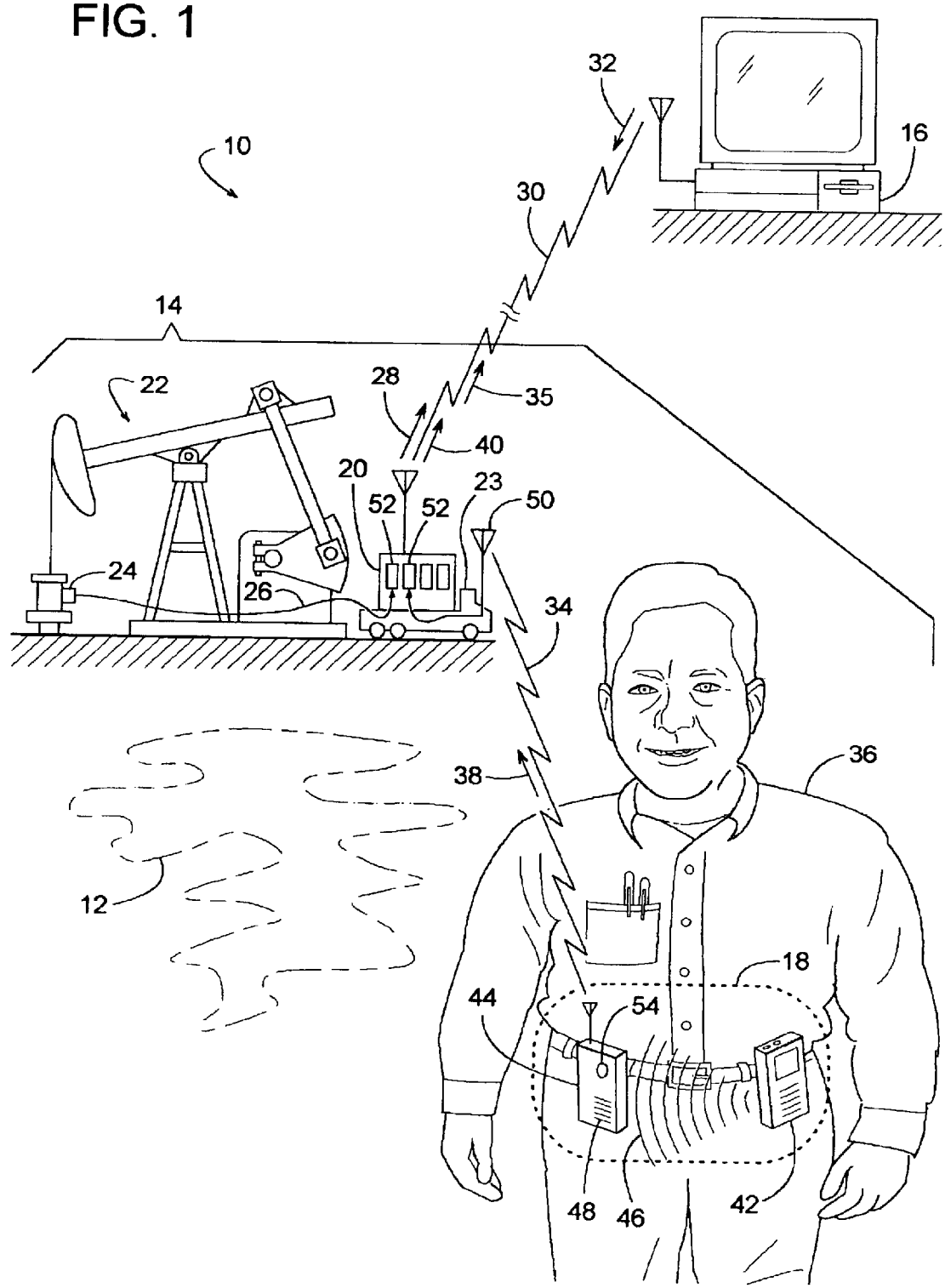
FIG. 1 is a schematic diagram showing a personal alarm system for responding to hydrogen sulfide gas at a well site.

FIG. 1 is a schematic diagram illustrating a personal alarm system 10 for detecting hydrogen sulfide gas 12 at a well site 14, which is at a remote location relative to a host computer 16. The term, "remote" refers to a distance of at least ten miles.

Alarm system 10 comprises a person-carried alarm instrument 18 and a fault monitoring system 20, wherein fault monitoring system 20 is placed (e.g., mounted, parked, installed, set up, etc.) at a generally fixed location at well site 14. System 20 can be any electrical system for receiving, storing and transmitting electrical signals. In some embodiments, fault monitoring system 20 is a conventional SCADA (Supervisory Control And Data Acquisition) system for monitoring and recording the conditions of a well-related operation 22 at well site 14 and making the stored monitored information, particularly well-related faults, available to host computer 16. A pressure sensor 24, for example, may send an operational fault signal 26 when the pumping pressure (or other operational characteristic, such as flow rate, temperature, liquid level, strain, load, etc.) at well site 14 is abnormal. Well-related operation 22 is schematically illustrated to represent operations that include, but are not necessarily limited to, producing gas, water or petroleum; repairing a well; servicing a well; inspecting a well; etc. In some cases, a service vehicle 23 can be used to help facilitate performing well-related operation 22 and can be used to transport system 20 to well site 14.

In cases where conventional SCADA software is used, host computer 16 accesses the stored monitored information by pinging system 20, whereby an alarm status signal 28 corresponding to fault signal 26 is conveyed to host computer 16 via a wireless communication link 30. Computer 16 can ping fault monitoring system 20 by sending an inquiry signal 32 to system 20 via wireless communication link 30. Inquiry signal 32 and the pinging process enables computer 16 to access well-related data of a particular well site that is at a location known to computer 16.

In other cases, however, fault monitoring system 20 provides alarm signal 28 over wireless communication link 30 without having to first be pinged. In such cases, system 20 may also provide a well location signal 35 that indicates the location of well site 14. Well location signal 35 can be in the form of an address, APIN or well number, or a gps reading (coordinates of a conventional global positioning system). Host computer 16 is thus informed of the H2S fault and its location.

Another wireless communication link 34 places fault monitoring system 20 in communication with person-carried alarm instrument 18. The term, "person-carried" refers to an item having one or more features that makes the item readily carried by a person. Such person-carried features include, but are not limited to, a belt clip, pocket clip, strap, compact size, lightweight, etc. Alarm instrument 18 is shown being carried by an oilfield worker 36, so instrument 18 actually travels or moves relative to fault monitoring system 20.

Upon sensing that a concentration of hydrogen sulfide gas 12 has reached a predetermined limit (e.g., 10 ppm), person-carried alarm instrument 18 provides a trigger signal 38. Wireless communication link 34 conveys trigger signal 38 to fault monitoring system 20, and fault monitoring system 20, in turn, provides an alarm status signal 40. The other wireless communication link 30 then conveys alarm status signal 40, and in some cases well location signal 35 and well-related operation data such as alarm status signal 28, to one or more designated host computers 16. In some embodiments, alarm status signals 28 and 40 are both communicated to computer 16 upon computer 16 pinging fault monitoring system 20. Alarm status 40 corresponds to trigger signal 38, so host computer 16 is notified that a hydrogen sulfide gas problem has occurred at well site 14. Thus, host computer 16 can be used for dispatching assistance to well site 14.

Wireless communication link 34 can be of various forms including, but not limited to, radio waves, infrared, spread spectrum, etc. Communication link 34 can have a range of a few hundred feet, which is appreciably less than that of communication link 30. Communication link 30 has a range of several miles, which can be achieved using technology such as satellite communications, radio waves, cell phone technology, etc. In some embodiments, communication with one or more host computers 16 involves the use of the Internet.

Alarm instrument 18 can be a single unit or may comprise two separate units. With two separate units, alarm instrument 18 may comprise a conventional H2S monitor 42 and a signal relay unit 44 Signal relay unit 44 provides a way for a conventional H2S monitor to communicate with a conventional SCADA system, such as fault monitoring system 20. The functional relationships of fault monitoring system 20, H23 monitor 42, and signal relay unit 44 can be further understood with a description of their operation.

When H2S monitor 42 senses that the concentration of hydrogen sulfide gas 12 exceeds a predetermined allowable limit, monitor 42, being a conventional H2S monitor, sounds an audible alarm signal 46. Signal relay unit 44 includes a microphone 48 that detects alarm signal 46, and signal relay unit 44 responds by generating trigger signal 38. A receiver 50 associated with fault monitoring system 20 receives trigger signal 38 and responds by recording the event on fault monitoring system 20. The H2S fault is recorded or stored to ensure that the awareness of the event is not lost before computer 16 pings fault monitoring system 20 or before alarm status signal 40 is communicated to computer 16. For instance, if computer 16 only pings fault monitoring system 20 once every ten minutes, computer 16 should receive alarm status signal 40 even if alarm signal 46 were cleared prior to system 20 being pinged. The step of recording the event can be carried out by tripping a conventional latch relay or storing the event on some other type of a memory (e.g., integrated circuit) of system 20. Such a memory or latch relay is schematically illustrated by numeral 52.

Since existing conventional H2S monitors may provide different sounding alarm signals, signal relay unit 44 includes a learning mode 54 for teaching unit 44 to recognize the sound of a particular alarm signal and to distinguish that sound from other extraneous or background sounds. When operating in learning mode 54, signal relay unit 44 listens to alarm signal 46 and stores its various attributes, which may include, but are not limited to, pitch, volume, waveform, tone, pulsating pattern, etc. Afterwards, signal relay unit 44 is returned to its normal operating mode where unit 44 listens for the alarm signal it just learned to recognize while in its learning mode. Such a learning process is based on common voice recognition technology, which is practiced by Sensory, Inc. of Santa Clara, Calif.

In some cases, signal relay unit 44 can be taught to recognize several different audible alarm patterns. This allows unit 44 to be paired up with different models of H2S monitors without having to repeat the learning process for each individual H2S monitor. Signal relay unit 44 would then emit trigger signal 38 if any one of several known alarm patterns were detected.

Although the invention is described with reference to a preferred embodiment, it should be appreciated by those skilled in the art that other variations are well within the scope of the invention. Also, it should be noted that the various elements, such as those represented by numerals 16, 20, 22, 23, and 36 are drawn out of scale to show more or less detail depending on the need. Therefore, the scope of the invention is to be determined by reference to the claims, which follow.

I claim:

1. A personal alarm system for responding to hydrogen sulfide gas at a well site that is at a remote location relative to a host computer, comprising:
   a person-carried alarm instrument providing a trigger signal in response to a concentration of hydrogen sulfide gas reaching a predetermined limit;
   a fault monitoring system set up at a generally fixed location at the well site, wherein the person-carried alarm instrument is movable relative to the fault monitoring system;
   a first wireless communication link having a limited distance range between the person-carried alarm instrument and the fault monitoring system, wherein the first wireless communication link conveys the trigger signal from the person-carried alarm instrument to the fault monitoring system;
   an alarm status signal created by the fault monitoring system in response to receiving the trigger signal from the person-carried alarm instrument; and
   a second wireless communication link having a greater distance range between the fault monitoring system and the host computer, wherein the greater distance range is greater than the limited distance range, and wherein the second wireless communication link conveys the alarm status signal from the fault monitoring system to the host computer, whereby the host computer is notified that the concentration of hydrogen sulfide gas reached the predetermined limit at the well site.

2. The personal alarm system of claim 1, wherein the person-carried alarm instrument includes an H2S monitor and a signal relay unit, and further comprising an alarm signal generated by the H2S monitor in response to the H2S monitor detecting that the concentration of hydrogen sulfide gas has reached the predetermined limit, wherein the signal relay unit provides the trigger signal in response to detecting that the H2S monitor generated the alarm signal.

3. The personal alarm system of claim 2, wherein the signal relay unit includes a microphone and the alarm signal is audible, whereby the signal relay unit uses the microphone to detect that the H2S monitor generated the alarm signal.

4. The personal alarm system of claim 3, wherein the signal relay unit includes a learning mode, wherein the signal relay unit learns and distinguishes the alarm signal from other background sounds.

5. The personal alarm system of claim 1, further comprising an inquiry signal periodically conveyed from the host computer to the fault monitoring system, wherein the alarm status signal is inhibited from being conveyed to the host computer until the inquiry signal is conveyed to the fault monitoring system.

6. The personal alarm system of claim 1, wherein the fault monitoring system includes a memory that remembers that the person-carried alarm instrument provided the trigger signal even after the trigger signal is discontinued.

7. The personal alarm system of claim 1, wherein the fault monitoring system monitors a plurality of potential faults at the known well site, wherein the plurality of potential faults includes the concentration of hydrogen sulfide gas reaching the predetermined limit.

8. A personal alarm system for responding to hydrogen sulfide gas at a known well site that is at a remote location relative to a host computer, wherein a well-related operation may occur at the known well site, the personal alarm system comprising:

a person-carried alarm instrument providing a trigger signal in response to a concentration of hydrogen sulfide gas reaching a predetermined limit;

a fault monitoring system set up at a generally fixed location at the known well site to monitor the well-related operation, wherein the person-carried alarm instrument is movable relative to the fault monitoring system;

a first wireless communication link having a limited distance range between the person-carried alarm instrument and the fault monitoring system, wherein the first wireless communication link conveys the trigger signal from the person-carried alarm instrument to the fault monitoring system;

a memory included with the fault monitoring system, wherein the fault monitoring system remembers receiving the trigger signal even after the trigger signal is discontinued;

an alarm status signal created by the fault monitoring system in response to receiving the trigger signal from the person-carried alarm instrument;

an inquiry signal periodically conveyed from the host computer to the fault monitoring system; and a second wireless communication link having a greater distance range between the fault monitoring system and the host computer, wherein the greater distance range is greater than the limited distance range, and wherein the second wireless communication link conveys the alarm status signal from the fault monitoring system to the host computer in response to the fault monitoring system receiving the inquiry signal from the host computer, whereby the host computer is notified that the concentration of hydrogen sulfide gas reached the predetermined limit at the known well site.

9. The personal alarm system of claim 8, wherein the memory includes a latch relay.

10. The personal alarm system of claim 8, wherein the person-carried alarm instrument includes an H2S monitor and a signal relay unit, and further comprising an alarm signal generated by the H2S monitor in response to the H2S monitor detecting that the concentration of hydrogen sulfide gas has reached the predetermined limit, wherein the signal relay unit provides the trigger signal in response to detecting that the H2S monitor generated the alarm signal.

11. The personal alarm system of claim 10, wherein the signal relay unit includes a microphone and the alarm signal is audible, whereby the signal relay unit uses the microphone to detect that the H2S monitor generated the alarm signal.

12. The personal alarm system of claim 10, wherein the signal relay unit includes a learning mode, wherein the signal relay unit learns to recognize the alarm signal so the signal relay unit can later distinguish the alarm signal from other background sounds.

13. The personal alarm system of claim 8, wherein the well-related operation involves conveying a fluid.

14. A method for responding to hydrogen sulfide gas at a well site that is at a remote location relative to a host computer, the method comprising:

placing a fault monitoring system at a generally fixed location at the well site;

performing a well-related operation at the well site;

generating a fault signal in response to an operational fault occurring with the well-related operation;

communicating the fault signal to the fault monitoring system;

providing a person-carried alarm instrument at the well site, wherein the person-carried alarm instrument provides a trigger signal in response to sensing a concentration of hydrogen sulfide gas has reached a predetermined limit;

carrying the person-carried alarm instrument at the well site, whereby the person-carried alarm instrument travels relative to the fault monitoring system;

communicating via a first wireless communication link the trigger signal from the person-carried alarm instrument to the fault monitoring system; and communicating via a second wireless communication link a first alarm status signal and a second alarm status signal from the fault monitoring system to the host computer, wherein the first alarm status signal corresponds to the fault signal of the well-related operation and the second alarm status signal corresponds to the trigger signal of the person-carried alarm instrument.

15. The method claim 14, wherein the person-carried alarm instrument includes an H2S monitor and a signal relay unit, and further comprising generating an audible alarm via the H2S monitor, and conveying the audible alarm from the H25 monitor to the signal relay unit, wherein the signal relay unit provides the trigger signal in response to receiving the audible alarm signal from the H25 monitor.

16. The method of claim 15, further comprising teaching the signal relay unit to recognize the audible alarm generated by the H2S monitor.

17. The method of claim 14, further comprising pinging the fault monitoring system via the host computer, wherein the step of communicating the first alarm status signal and the second alarm status signal is performed in response to the step of pinging the fault monitoring system.

18. The method of claim 14, further comprising via the fault monitoring system remembering the occurrence of the fault signal even after the fault signal is discontinued.

19. The method of claim 14, further comprising via the fault monitoring system remembering the occurrence of the trigger signal even after the trigger signal is discontinued.

20. A method for responding to hydrogen sulfide gas at a well site that is at a remote location relative to a host computer, wherein a service vehicle facilitates performing a service operation at the well site, the method comprising:

using the service vehicle to transport a fault monitoring system to the well site;

parking the service vehicle at the well site, thereby placing the fault monitoring system at a generally fixed location at the well site;

performing the service operation at the well site;

providing a person-carried alarm instrument at the well site, wherein the person-carried alarm instrument provides a trigger signal in response to sensing a concentration of hydrogen sulfide gas has reached a predetermined limit;

carrying the person-carried alarm instrument at the well site, whereby the person-carried alarm instrument travels relative to the fault monitoring system which is at the generally fixed location;

communicating via a first wireless communication link the trigger signal from the person-carried alarm instrument to the fault monitoring system;

communicating via a second wireless communication link an alarm status signal from the fault monitoring system to the host computer, wherein the alarm status signal corresponds to the trigger signal of the person-carried alarm instrument; and communicating via the second wireless communication link a well location signal from the fault monitoring system to the host computer, wherein the well location signal identifies the remote location of the well site, whereby the host computer is notified that the concentration of hydrogen sulfide gas reached the predetermined limit at the remote location of the well site.

* * * * *